(12) United States Patent
Ellman et al.

(10) Patent No.: US 6,306,135 B1
(45) Date of Patent: Oct. 23, 2001

(54) FOREHEAD LIFT SUCTION PROBE

(76) Inventors: Alan G. Ellman; Jon C. Garito, both of 1135 Railroad Ave., Hewlett, NY (US) 11557

(*) Notice: Subject to any disclaimer, the term of this patent is extended or adjusted under 35 U.S.C. 154(b) by 0 days.

(21) Appl. No.: 09/442,315

(22) Filed: Nov. 22, 1999

(51) Int. Cl.$^7$ .................................................. A61B 18/18
(52) U.S. Cl. ............................... 606/45; 606/46; 606/48
(58) Field of Search .................................. 606/22, 32, 9, 606/41, 46, 48; 128/898; 604/22, 20

(56) References Cited

U.S. PATENT DOCUMENTS

| | | | |
|---|---|---|---|
| 3,974,833 | * | 8/1976 | Durden, III .............................. 604/20 |
| 5,196,007 | | 3/1993 | Ellman et al. . |
| 5,395,312 | * | 3/1995 | Desia ..................................... 604/22 |
| 5,452,732 | * | 9/1995 | Bircoll .................................. 128/898 |
| 5,486,161 | * | 1/1996 | Laz et al. ............................... 604/22 |
| 5,496,314 | * | 3/1996 | Eggers ................................... 606/41 |
| 5,549,625 | * | 8/1996 | Bircoll ................................. 606/192 |
| 5,733,283 | * | 3/1998 | Malis et al. ............................ 606/48 |
| 5,746,762 | * | 5/1998 | Bass ..................................... 606/192 |
| 5,766,167 | * | 6/1998 | Eggers et al. ......................... 606/46 |
| 5,785,705 | * | 7/1998 | Baker .................................... 606/32 |
| 5,807,385 | * | 9/1998 | Keller ..................................... 606/9 |
| 5,830,214 | * | 11/1998 | Flom et al. ............................ 606/41 |
| 5,935,142 | * | 8/1999 | Hood ................................... 606/169 |
| 5,950,633 | * | 9/1999 | Lynch et al. ......................... 128/898 |
| 6,139,559 | * | 10/2000 | Nordan et al. ....................... 606/166 |

OTHER PUBLICATIONS

Endoscopic Plastic Surgery, by Bostwick III, Eaves III, and Nahi, published 1995 by Quality Medical Publishing, Inc. of St. Louis, Missouri, pp. 166–170.

* cited by examiner

*Primary Examiner*—Michael Peffley

(57) ABSTRACT

An electrosurgical electrode for performing an ELF procedure comprises an elongated thin, electrically-conductive tube shaped to substantially match the curvature of the skull extending from the brow upward to a position at or above the hairline. The electrically-conductive tube terminates at a distal end in a generally spade-shaped end with an opening whose tip is bare but of which the remainder of the spade-shaped end is covered with a thin coating of an electrically-insulating coating. The remainder of the electrically-conductive tube is also covered with an electrically-insulating coating. The proximal end of the electrically-conductive tube is connected to a handpiece whose interior is hollow and which can be connected to a flexible suction tube coupled to a source of suction. Connected to the handpiece is a connector which makes a good electrically-conductive contact to the electrically-conductive tube. The connector in turn is provided with a cable that can be plugged into conventional electrosurgical apparatus. During the part of the procedure when a muscle is severed by activating the electrosurgical apparatus, the suction source can also be activated to remove any smoke or plumes that can interfere with a surgeons view of the cutting action.

16 Claims, 2 Drawing Sheets

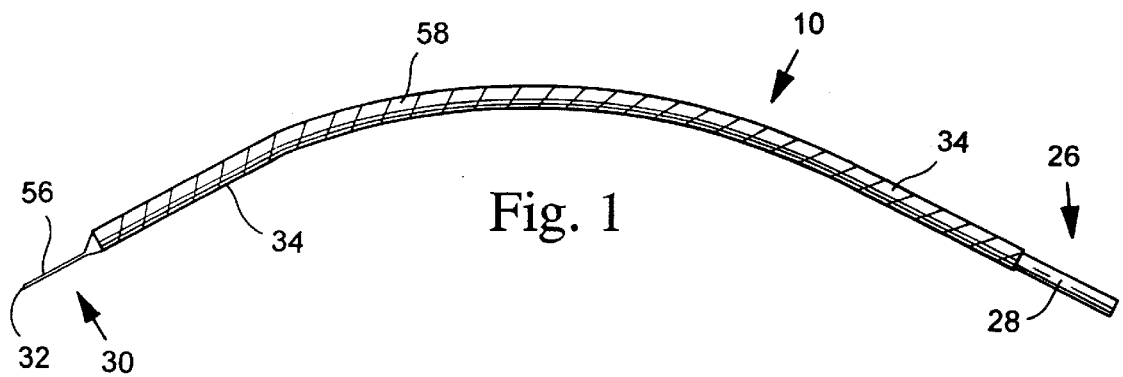
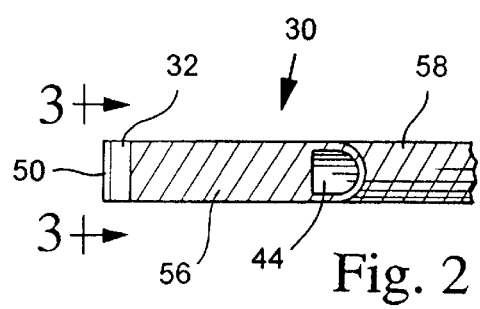
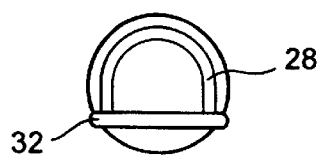
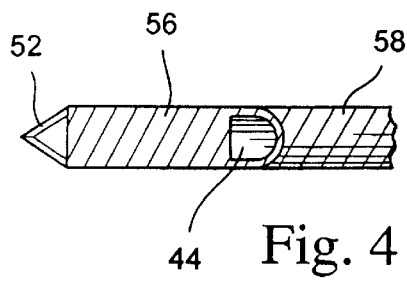
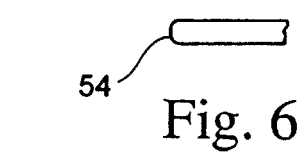
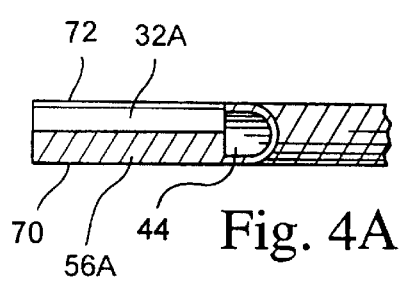
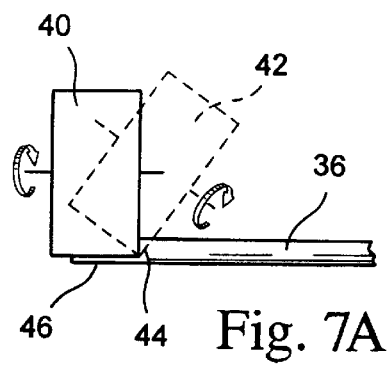
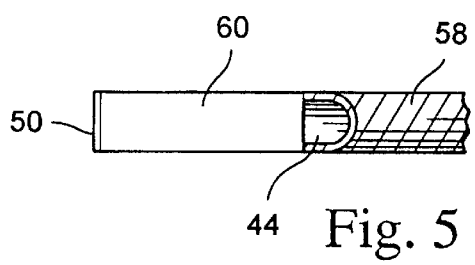
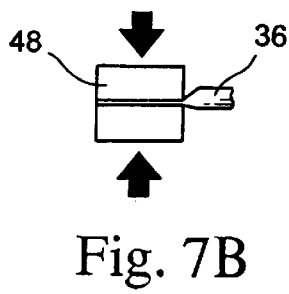

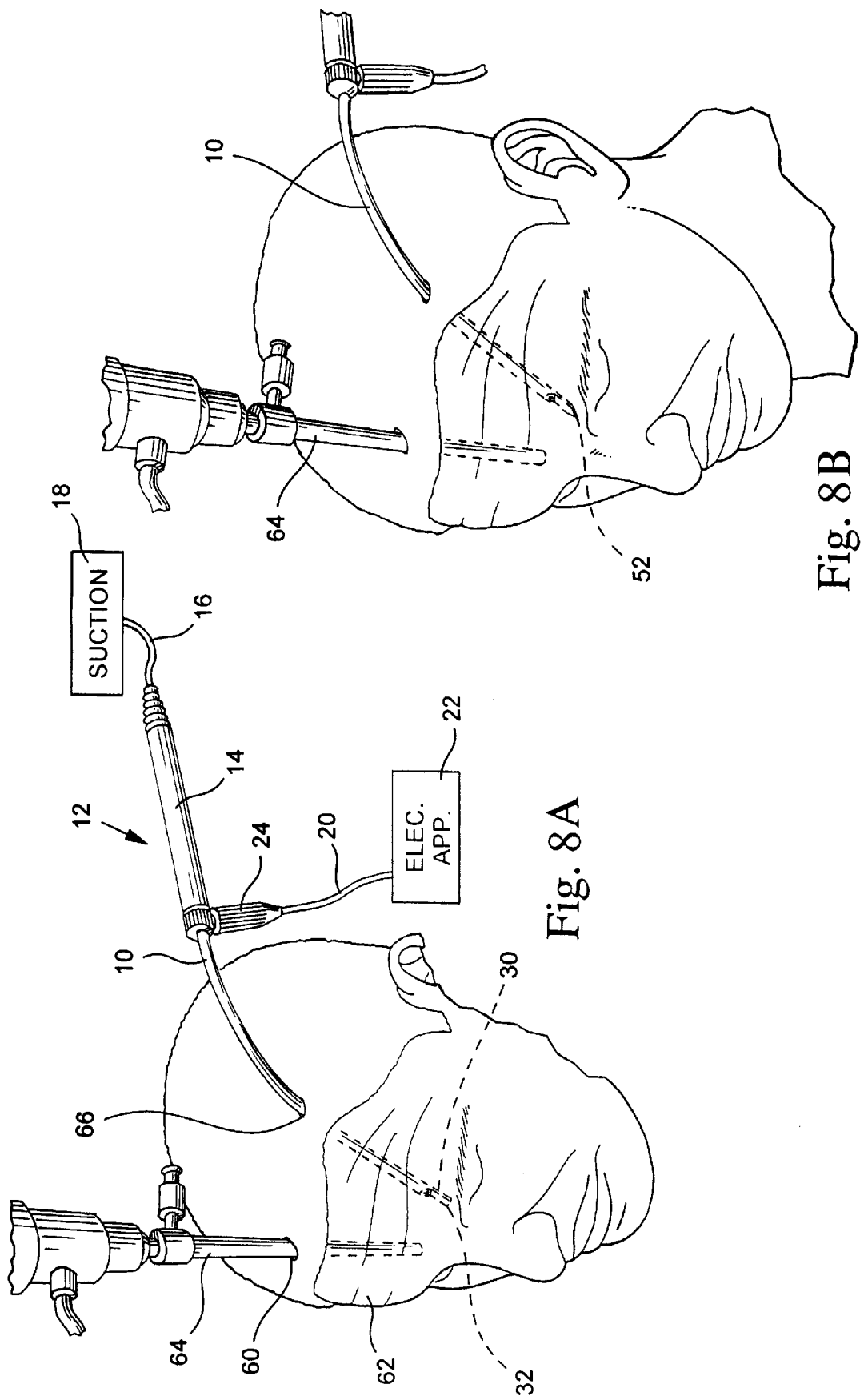

FOREHEAD LIFT SUCTION PROBE

This invention relates to an electrosurgical electrode, and in particular to an electrosurgical electrode for performing a surgical procedure known as an Endoscope Forehead Lift (EFL).

BACKGROUND OF THE INVENTION

In the EFL procedure that is pertinent to this invention, via endoscopic visualization, a muscle extending over the brow and contributing to skin wrinkling due to excessive pulling forces on the skin is severed at least in part. Access to the muscle is obtained via a hole formed in the scalp at a position about three or so inches above the brow, and extending a probe with a thin edge through the hole and down via a tunnel forced between the scalp and the skull to the muscle to sever part or all of the same. If properly done, this should relieve the excessive pulling forces tending to smooth the forehead skin. See "Endoscopic Plastic Surgery", by Bostwick III, Eaves III, and Nahai, published by Quality Medical Publishing, Inc. of St. Louis Mo., 1995, Pgs. 166–170, the contents of which are hereby incorporated by reference, for a description of the procedure and how it works.

SUMMARY OF THE INVENTION

The present invention describes a novel electrosurgical electrode that can be used to perform the EFL and similar procedures simpler and with fewer side effects than other techniques.

Briefly stated, the novel electrode comprises an elongated thin, electrically-conductive tubular member shaped to substantially follow the curvature of the skull extending from the brow upward to a position at or above the hairline. The electrically-conductive tubular member terminates at a distal end in a generally spade-shaped end whose tip is bare. The remainder of the electrically-conductive tubular member is covered with an electrically-insulating coating. The proximal end of the electrically-conductive tubular member is connected to a handpiece whose interior is hollow and which can be connected to a flexible suction tube coupled to a source of suction. Also connected to the handpiece is a connector which makes a good electrically-conductive contact to the electrically-conductive tubular member. The connector in turn is provided with a cable that can be plugged into conventional electrosurgical apparatus. During the part of the procedure when the muscle is severed by activating the electrosurgical apparatus, the suction source can also be activated to remove any smoke or vapor that can interfere with the surgeon's view of the cutting action.

In a preferred embodiment, most of the spade-shaped end, both sides and edges, adjacent the tubular member is covered with a thin coating of an electrically-insulating coating leaving only a bare tip capable of supplying electrosurgical currents to tissue.

The handpiece can be of the type described in our U.S. Pat. No. 5,196,007, whose contents are hereby incorporated by reference, and which describes a handpiece which combines electrosurgical currents at a working end of an electrode together with suction at the same working end supplied via a hollow handpiece. The patent nowhere describes its application to the EFL procedure, and the electrodes described in the patent are not suitable for carrying out the EFL procedure.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention.

BRIEF DESCRIPTION OF THE DRAWINGS

In the drawings:

FIG. 1 is a side view of one form of an electrode in accordance with the invention;

FIG. 2 is an enlarged top view of the working end of the electrode of FIG. 1;

FIG. 3 is an enlarged end view of the working end of the electrode of FIG. 1 taken along the line 3—3;

FIGS. 4, 4A, and 5 are enlarged top views of the working end of modified forms of an electrode according to the invention;

FIG. 6 is a top view of the working end of another modified form of an electrode according to the invention;

FIGS. 7A and 7B are schematic views illustrating how the electrode depicted in FIG. 1 can be manufactured;

FIGS. 8A and 8B are schematic views illustrating how the electrode of FIG. 1 can be used to perform an ELF procedure.

DETAILED DESCRIPTION OF THE PREFERRED EMBODIMENTS

FIG. 1 is a side view of one form of an electrode 10 in accordance with the invention. FIG. 8A shows the electrode of FIG. 1 mounted in a suction handpiece 12 of the type described and illustrated in U.S. Pat. No. 5,196,007. The reader is directed to the referenced patent for the details of the handpiece 12 which will assist in understanding its internal construction and how the electrode 10 is held and supplied with suction when desired. Suffice to say for present purposes, the handpiece handle 14 is hollow and is connected at its right end to a suction hose 16 (see FIG. 8A) connected to a suitable source 18 of suction. A cable 20 connected to a suitable source 22 of electrosurgical currents is connected at the left hand side of the handpiece 12 via a connector 24 to an internal electrically-conductive tube (not shown) which can receive and hold and electrically connect to the bare shank end 26 of the electrode 10 and which can also convey the suction to the left hand side of the handpiece and the electrode.

The electrode 10 shown in FIG. 1 comprises a hollow tubular member 28, for example of brass, which extends from the bare shank end 26 on the right side to a working end 30 on the left side of the figure having a bare tip 32. The working end 30 has a generally flat spade-like shape having preferably a width of about 0.1–0.2 inches, a length of about 0.5–0.9 inches, and a thickness of about 0.01–0.03 inches. The length of the bare tip 32 is about 0.04–0.2 inches. The length dimension is the dimension in the direction of the longitudinal or long axis of the electrode 10. The electrode 10 is made from a straight tube by bending about a mandrel having a radius of curvature of about 4.5 inches leaving two straight end sections 34. The overall length of the electrode 10 is about 5.5–8.5 inches.

A preferred way of fabricating the electrode 10 is illustrated in FIGS. 7A and 7D. The starting point is a stiff straight brass tube 36 of the required length. One end, left bare, serves as the shank 26. The other end is subjected to two cutting or grinding operations. The first, illustrated in FIG. 7A, grinds 40 straight down from the top to remove roughly ¼–½ inches of the tube end over a distance approximately equal to the length of the spade end. The second, also illustrated in FIG. 7A, grinds 42 at roughly a 45° angle to form a 45° slant at the remaining open end 44 of the tube. The slightly curved bottom part 46 of the tube end left is then flattened in a vise 48 as shown in FIG. 7B. Next, the free end of the resultant spade-shaped body may be bevelled to provide a bevelled edge as shown in FIG. 2 at 50, or alternatively bevelled as well as ground to a point as shown at FIG. 4 at 52. If desired the edges of the straight end can be rounded as shown at 54 in FIG. 6. Then an electrically-insulating coating 56 is deposited over all of the spade end except for the bare tip 32. With the pointed end 52, the coating 56 preferably covers up to the beginning of the point. Fused powdered Teflon can be used for this purpose. Next, a heat shrinkable plastic tube 58 is provided to encircle the entire length of the tube except for the spade end and the shank end 26. Finally, the electrode is bent around a mandrel to give it the final curved shape desired.

FIGS. 8A and 8B illustrate schematically how the electrode is used in conducting an ELF procedure, and the significance of the spade end construction and the shape and construction of the electrode will become clearer. In this procedure, only the steps to explain how the electrode 10 carries out its tasks are given, but it will be understood that many other steps having to do with preparing the patient and anchoring the forehead scalp after severing of the muscle have been omitted for brevity.

Essentially, the scalp is perforated 60 (also referred to as a central incision) above the brow 62, and an endoscope probe 64, as shown, inserted so that the surgeon can visualize the progress of the procedure. Typically, the blunt edge of the endoscope probe is then used with blunt dissection to move tissue to provide a space between the scalp and skull within which the electrode will be inserted and that will allow the surgeon to visualize the actions of the inserted electrode. Then the electrode 10 is inserted from above, typically by way of a lateral incision 66, and advanced down in the space between the scalp and the skull toward the brow 62 as shown. The electrode 10 is not activated, nor is the suction. By a process of blunt dissection using the front edge 50 of the electrode, as the surgeon advances the electrode 10, the tissues binding the scalp to the skull are displaced. This is continued until the muscle to be severed is reached, approximately 3–6 inches below the initial perforation. Then the suction 18 is energized providing suction at the open end 44 of the tubular member adjoining the spade end and the electrosurgical apparatus 22 is activated while the surgeon manipulates the electrode end with its bare tip 32 to sever the muscle by the emitted electrosurgical currents. The smoke or vapor generated by the electrically cut tissue, which would normally obstruct the surgeon's vision, is exhausted via the end tube opening 44 and the incorporated tube 28 inside the electrode 10 to the suction apparatus via the hollow handpiece 10. The electrode 10 may then be withdrawn and the rest of the procedure followed.

The advantages of the electrode of the invention in carrying out this procedure include: cutting of the muscle using electrosurgical currents will simultaneously allow coagulation of any bleeders; typically only a single instrument, the electrode of the invention, is needed, in contrast with the need to use a number of different instruments when an ordinary scalpel is used.

While the electrode described is particularly suitable for implementing the ELF procedure, those skilled in this art will recognize that other procedures that involve plastic surgery such as face or body lifts or other cosmetic procedures will also find the electrode of the invention helpful in reducing training time, reducing operative time, and thus reducing the cost of these surgical procedures.

In the preferred embodiment, the part of the spade-shaped end adjacent the cut end of the tubular member is coated with an electrically-insulating coating 56 leaving only the tip 32 bare for supplying electrosurgical currents to the tissue. In a modification that may find use in other similar procedures, the entire spade-end is left bare as illustrated at 60 in FIG. 5. The electrode otherwise is the same as that of FIG. 1. The darker areas adjacent the bare tip 32 in FIG. 1, designated 56 and 58, are used to represent the electrically-insulating coatings. FIG. 8B shows the use of the pointed end electrode 52 of FIG. 4 used in the described procedure. The front edge of both electrodes while thin is preferably not sharpened to a sharp cutting edge to avoid cutting the tissue holding the scalp to the skull when the electrode 10 is pushed down to the brow. The downward movement uses blunt dissection to move through the tissue.

In the preceding embodiments, the thin electrically-insulating coating 56 covers both of the flat sides where shown as well as the side edges of part of the spade-shaped end 30, the dividing line between the coated and bare sections extending transversely to the long axis of the electrode 10. FIG. 4A shows another preferred embodiment. In this case, the dividing line between the coated 56A and bare 32A sections extends parallel to the long axis of the electrode 10. The longitudinally-extending coated section 70 covers both sides and one edge of the spade-shaped end. The longitudinally-extending bare section 72, on both sides and the other edge, extends from the tip to the open bore 44. Thus, the electrosurgical currents are emitted from the bare side edge 32A of the electrode, thus allowing the surgeon to cut tissue with a sideways movement of the working end 30 of the electrode.

Any electrosurgical apparatus 22 can be used. A preferred apparatus is available from Ellman International of Hewlett, N.Y. as Model IEC50 or IEC100.

The insulating coatings 56, 58 will prevent accidental touching of patient tissue by the electrode sides, so that the electrosurgical currents are locallized to the bare electrode end 32.

The apparatus used in the procedure preferably generates electrosurgical currents with a frequency of about 2.5–4 MHz, with 4 MHz preferred.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical electrode for performing an EFL procedure on the forehead of a human patient wherein under endoscopic visualization an electrode inserted above the brow is forced through a space formed between the scalp and the skull until reaching a muscle extending over the brow and severing the muscle with electrosurgical currents supplied by electrosurgical apparatus connected to the electrode, the electrode comprising:

(a) an elongated electrically-conductive tubular member having at a first end means for connecting to electrosurgical apparatus and having at a second end a tip with an opening that serves as the working end of the electrode and adjacent the tip an electrode portion, (b) the electrode portion adjacent the tip being generally spade-shaped and comprising, in order, an electrically-conductive active first section and a second section, the first and second sections extending in a straight line aligned with the immediately-adjacent portion of the tubular member, (c) the active first section being bare so as to allow electrosurgical currents to enter contacted tissue when the electrosurgical apparatus is activated, (d) the second section having a thin electrically-insulating coating so as to prevent electrosurgical currents to enter contacted tissue when the electrosurgical apparatus is activated, (e) the tubular member comprising a duct leading to the opening for connection to a source of suction, (f) the tubular member having a generally curved shape that follows the curvature of the forehead of a patient such that the electrode can be inserted into the space between the scalp and skull at the forehead and advanced until a muscle under the brow is reached and the muscle severed with electrosurgical currents by activating the electrosurgical apparatus while activating the source of suction to remove any smoke or plume.

2. The electrosurgical electrode as claimed in claim 1, wherein the spade-shaped electrode portion is an integral extension of the tubular member made by at least a cutting step such that the tubular end adjacent the cut provides the opening that remains unobstructed for the flow of suction.

3. The electrosurgical electrode as claimed in claim 1, wherein the overall length of the tubular member is about 5.5–8.5 inches.

4. The electrosurgical electrode as claimed in claim 1, wherein the tubular member comprises straight end sections and a curved center section having a radius of curvature of about 3.5–5.5 inches.

5. The electrosurgical electrode as claimed in claim 1, wherein the tubular member is made of brass.

6. The electrosurgical electrode as claimed in claim 1 wherein the spade-shaped end has a width of about 0.1–0.2 inches.

7. The electrosurgical electrode as claimed in claim 1 wherein the first section of the spade-shaped end has a length of about 0.04–0.2 inches.

8. The electrosurgical electrode as claimed in claim 1, wherein the second section of the spade-shaped end has a length of about 0.5–0.9 inches.

9. The electrosurgical electrode as claimed in claim 1, wherein the first section has a tip that is beveled but blunt.

10. The electrosurgical electrode as claimed in claim 1, wherein the first section has a tip that is straight or pointed or rounded.

11. The electrosurgical electrode as claimed in claim 1, wherein the second section is separated from the first section by a dividing line extending transversely to a long axis of the electrode.

12. The electrosurgical electrode as claimed in claim 1, wherein the second section is separated from the first section by a dividing line extending parallel to a long axis of the electrode.

13. The method for making an electrosurgical electrode for performing an ELF procedure on the forehead of a patient, said electrosurgical electrode comprising:

(a) an elongated electrically-conductive tubular member having at a first end means for connecting to the first means of the handpiece and having at a second end a tip with an opening that serves as the working end of the electrode and adjacent the tip an electrode portion, (b) the electrode portion adjacent the tip being generally spade-shaped and comprising, in order, an electrically-conductive active first section and an electrically-insulated second section, (c) the active first section being bare so as to allow electrosurgical currents to enter contacted tissue when the electrosurgical apparatus is activated, (d) the second section having a relatively thin electrically-insulating coating so as to prevent electrosurgical currents to enter contacted tissue when the electrosurgical apparatus is activated, (e) said method comprising:
  i) providing an elongated metal tube,
  ii) cutting the end of the tube transversely and at an angle to form the generally spade-shaped working end with the opening,
  iii) providing an electrically-insulating coating over the elongated metal tube and the spade-shaped working end except for a small part adjacent the tip,
  iv) shaping the elongated metal tube to follow the contour of the forehead of a patient.

14. The method of claim 13, wherein, following step (e)(ii), the cut end is subjected to a flattening operation.

15. A method for performing an electrosurgical EFL procedure on the forehead of a human patient, comprising the steps:

A) inserting an endoscopic probe into a space formed between the scalp and the skull for visualizing muscle tissue extending over the brow, B) providing a source of suction, C) providing electrosurgical apparatus for generating electrosurgical currents and an electrosurgical electrode connected to the apparatus and comprising:

(a) an elongated electrically-conductive tubular member having at a first end means for connecting to the electrosurgical apparatus and having at a second end a tip with an opening that serves as the working end of the electrode and adjacent the tip an electrode portion, (b) the electrode portion adjacent the tip being generally spade-shaped and comprising, in order, an electrically-conductive active first section and a second section, the first and second sections extending in a straight line aligned with the immediately-adjacent portion of the tubular member, (c) the active first section being bare so as to allow electrosurgical currents to enter contacted tissue when the electrosurgical apparatus is activated, (d) the second section having a relatively thin electrically-insulating coating so as to prevent electrosurgical currents to enter contacted tissue when the electrosurgical apparatus is activated, (e) the tubular member comprising a duct leading to the opening for connection to the source of suction, (f) the tubular member having a generally curved shape that follows the curvature of the forehead of the patient, D) using blunt dissection inserting the electrode from above the brow into the space formed between the scalp and the skull until reaching the muscle tissue extending over the brow.

E) activating the electrosurgical apparatus and the source of suction and cutting the muscle tissue with electrosurgical currents from the active first section while suction is provided within the space via the opening to remove any plumes resulting from cutting of the tissue.

16. The electrosurgical electrode as claimed in claim 15, wherein the overall length of the tubular member is about 5.5–8.5 inches.

* * * * *